United States Patent [19]

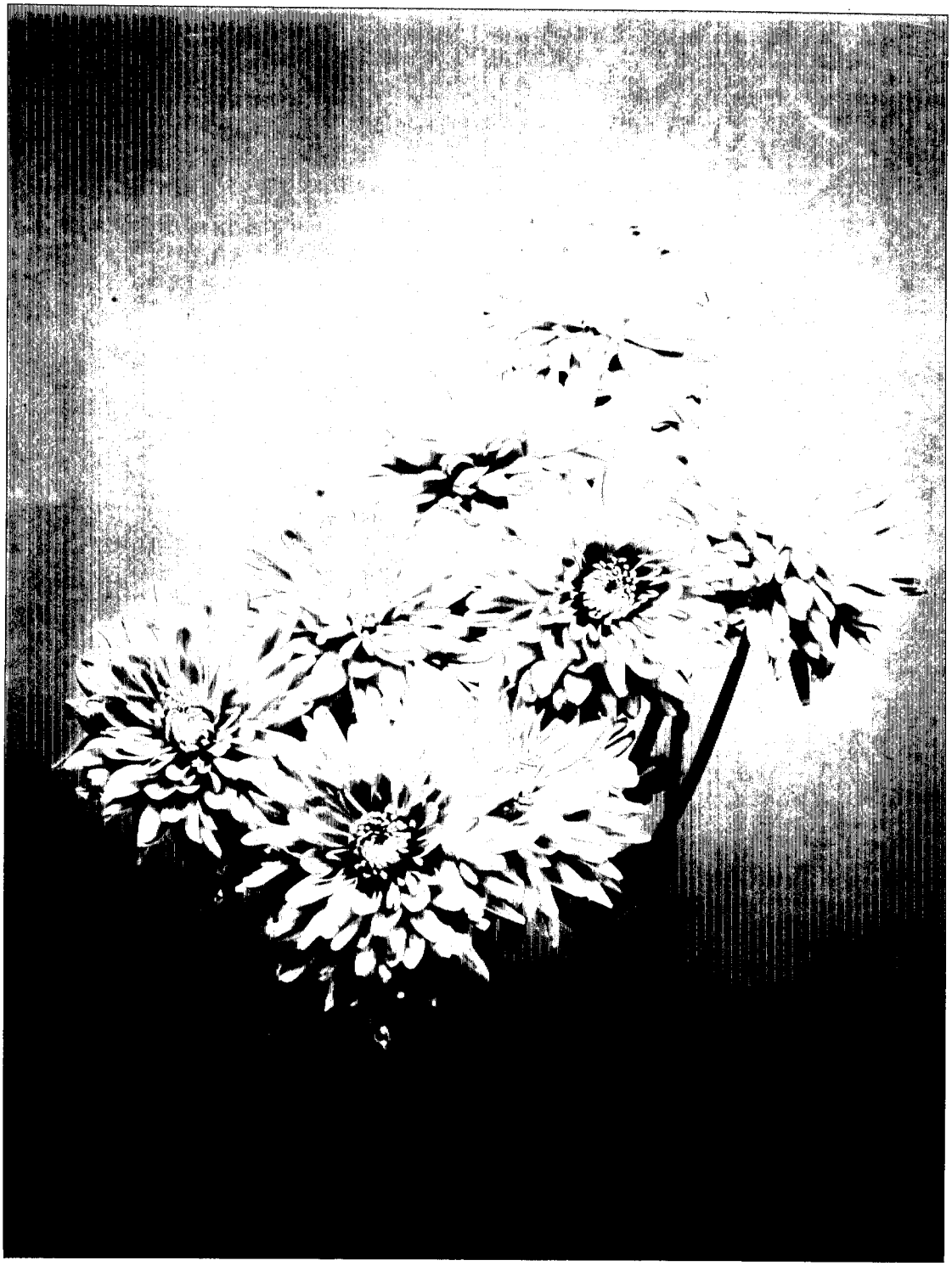

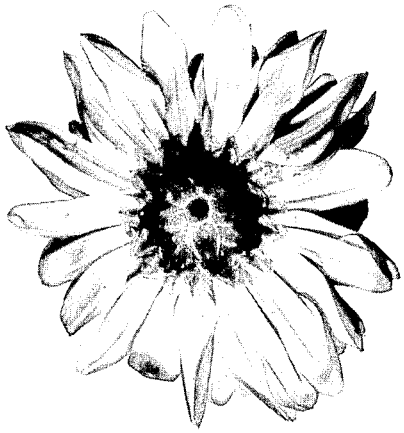
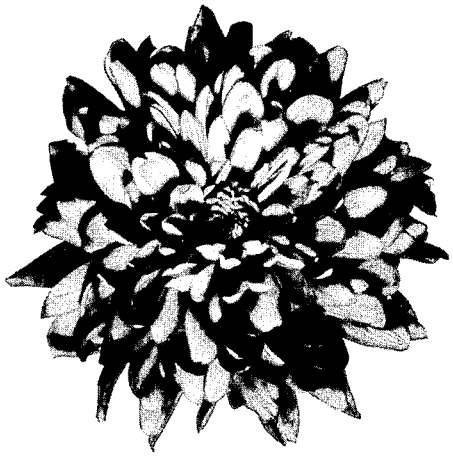
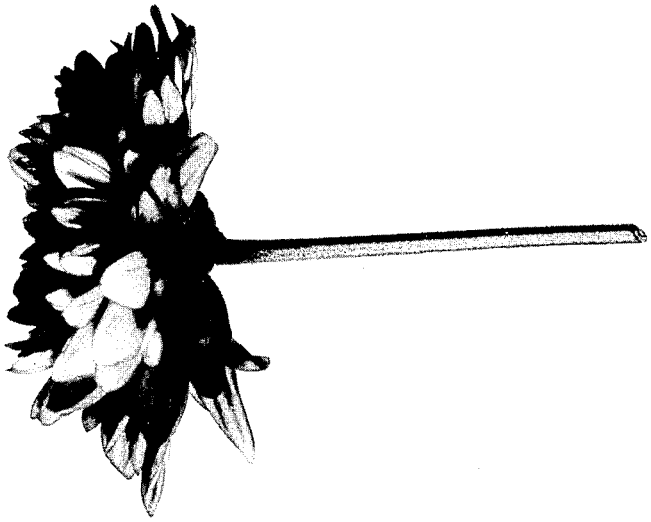

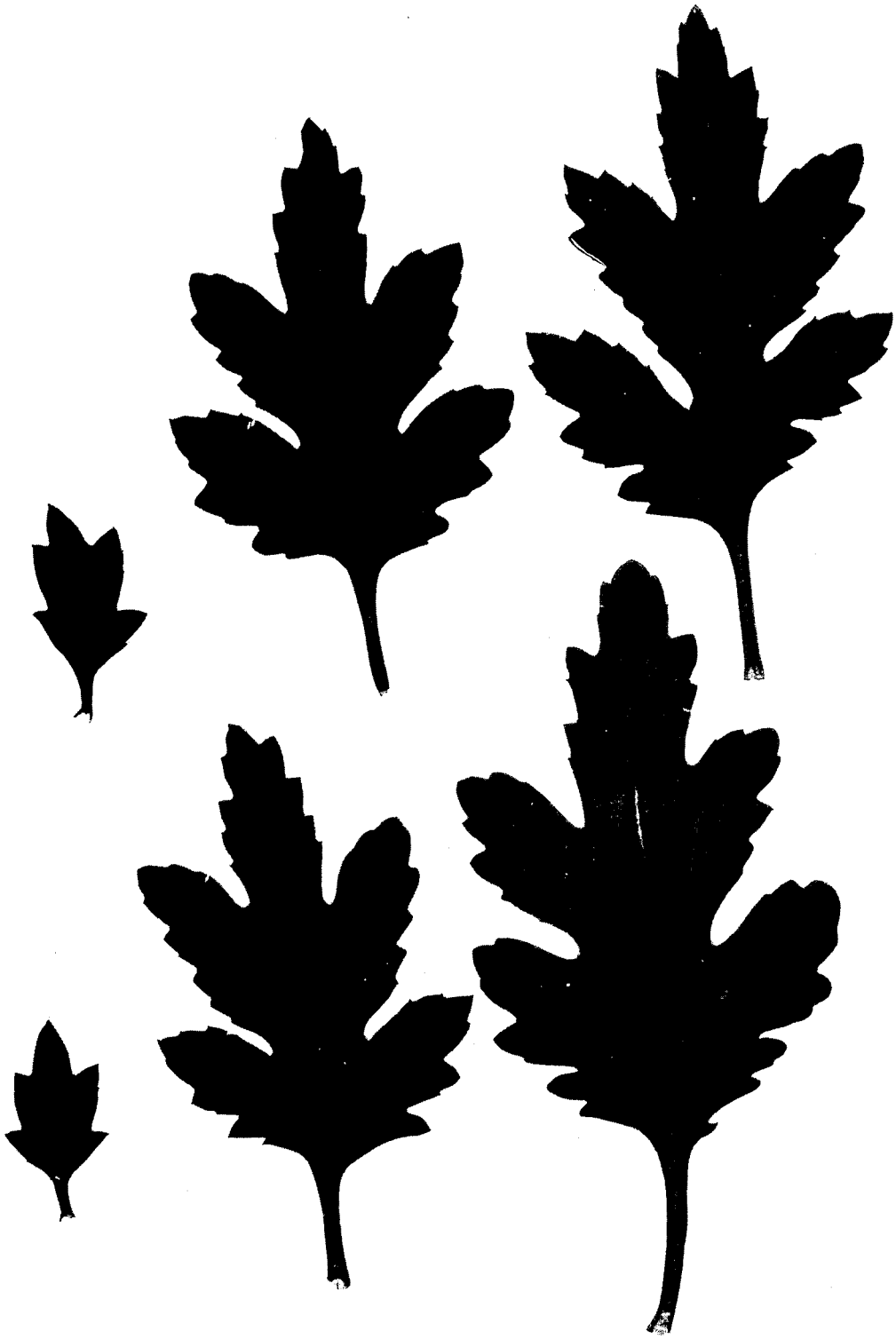

Duffett

[11] Patent Number: Plant 5,748

[45] Date of Patent: May 13, 1986

[54] CHRYSANTHEMUM PLANT NAMED BRASS

[75] Inventor: William E. Duffett, Salinas, Calif.

[73] Assignee: Yoder Brothers, Inc., Barberton, Ohio

[21] Appl. No.: 644,269

[22] Filed: Aug. 27, 1984

[51] Int. Cl.[4] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant names Brass characterized as to uniqueness by the combined characteristics of flat capitulum form, decorative capitulum type, greyed-orange ray floret color, diameter across face of capitulum ranging from 6 to 7 cm. at maturity, uniform nine week flowering response, medium plant height when grown single stem, 10 to 15 cm. peduncles on open, normally terminal sprays, and 13° C. minimum temperature tolerance for initiation and development of flowering buds.

3 Drawing Figures

The present invention comprises a new and distinct cultivar of *Chrysanthemum morifolium,* Ramat., named Brass.

Brass is a product of a planned breeding program which had the objective of creating new chrysanthemum cultivars having low temperature tolerance for cut spray mum programs with decorative capitulum type, bronze ray floret color, eight to nine week flowering response, and the ability to produce commercially acceptable quality in year round programs. Such traits in combination were not present or needed improvement in previously available commercial cultivars.

Brass, identified as 78768001, was originated from a cross made by William E. Duffett in a controlled breeding program in Salinas, Calif. in 1977. The female parent was the yellow decorative cultivar identified as 7030202 and named Solarama, disclosed by U.S. Plant Pat. No. 3,673. The male parent of Brass was the bronze daisy cultivar identified as 72097002 and named Tantalizer, disclosed by U.S. Plant Pat. No. 3,906.

Brass was discovered and selected as one flowering plant within the progeny of the stated cross by William E. Duffett on Aug. 22, 1978 in a controlled environment in Salinas, Calif.

The first act of asexual reproduction of Brass was accomplished when vegetative cuttings were taken from the initial selection in Nov. 1978 in a controlled environment in Salinas, Calif. by a technician working under formulations established and supervised by William E. Duffett.

Horticultural examination of selected units initiated Feb. 1979 has demonstrated that the combination of characteristics as herein disclosed for Brass are firmly fixed and are retained through successive generations of asexual reproduction.

Brass has not been observed under all possible environmental conditions. The phenotype may vary significantly with variations in environment such as temperature, light intensity and day length. The following observations, measurements and comparisons describe plants grown in Salinas, Calif. and Bogota, Colombia under greenhouse conditions which approximate those generally used in commercial practice.

The following traits have been repeatedly observed and are determined to be basic characteristics of Brass which in combination distinguish this chrysanthemum as a new and distinct cultivar:

(1) Flat capitulum form.

(2) Decorative capitulum type.

(3) Greyed-orange ray floret color.

(4) Diameter across face of capitulum ranging from 6 to 7 cm. at maturity.

(5) Uniform nine week photoperiodic flowering response to short days.

(6) Medium peduncle length, ranging from 10 to 15 cm.

(7) Medium plant height, requiring 2 to 3 long day weeks prior to short days to attain a flowered plant height of 100 to 110 cm. for April through November Salinas, Calif. flowering; and year around flowering in Bogota, Colombia.

(8) Low temperature tolerance of 13° C. for initiation and development when grown in single stem cut spray programs with a continuous dark period of 12 to 13 hours.

The accompanying photographic drawings show typical inflorescence and leaf characteristics of Brass, with the colors being as nearly true as possible with illustrations of this type. Sheet 1 is a color photograph of Brass grown as a single stem cut spray. Sheet 2 is a black and white photograph of three views of the inflorescence of Brass. Sheet 3 is a black and white photograph showing upper and under surfaces of the leaves of Brass at three stages of development (mature, intermediate and immature).

Of the many commercial cultivars known to the present inventor, the most similar in comparison to Brass is Flame Belair, disclosed in U.S. Plant Pat. No. 3,353. Reference is made to attached Chart A which compares certain characteristics of Brass to those same characteristics of Flame Belair. In comparison to Flame Belair, Brass has darker inflorescence color, smaller capitulum diameter, shorter peduncle length, shorter plant height, and lower temperature tolerance for bud initiation. The capitulum type and form, and response to controlled short days are similar for both cultivars.

In the following description, color references are made to The Royal Horticultural Society Colour Chart. The color values were determined between 9:30 A.M. and 9:45 A.M. on Jan. 6, 1984 under 380 foot-candle light intensity at Salinas, Calif.

Classification:

*Botanical.*—*Chrysanthemum morifolium,* Ramat., cv BRASS.

*Commercial.*—Decorative spray cut mum.

I. INFLORESCENCE

A. Capitulum:

*Form.*—Flat.

*Type.*—Decorative.

*Diameter across face.*—6 to 7 cm.

B. Corolla of ray florets:

*Color (general tonality from a distance of three meters).*—Greyed-orange.

*Color (upper surface).*—168A, B and C.

*Color (under surface).*—163B, C.

*Shape.*—Oblong. Rounded tip.

C. Corolla of disc florets:

*Color (mature).*—2B.

*Color (immature).*—154A.

D. Reproductive organs:

*Androecium.*—Present disc florets only; scant pollen.

*Gynoecium.*—Present both ray and disc florets.

II. PLANT

A. General appearance:

*Height.*—Medium; 100 to 110 cm., as a single stem flowering plant from a rooted cutting, with fourteen long days for April through November flowerings and maintaining a minimum nightly 12 to 13 hour continuous dark period.

B. Foliage:

*Color (upper surface).*—147A.

*Color (under surface).*—147B.

*Shape.*—Deeply lobed and moderately serrated.

CHART A

COMPARISON OF BRASS AND FLAME BELAIR

| CULTIVAR | RAY FLORET COLOR | CAPITULUM FORM AND TYPE | SPRAY FORMATION | DIAMETER ACROSS FACE OF CAPITULUM |
|---|---|---|---|---|
| BRASS | GREYED-ORANGE | FLAT DECORATIVE | 10 to 15 cm. PEDUNCLES | 6 to 7 cm. |
| FLAME BELAIR | ORANGE | FLAT DECORATIVE | 15 to 20 cm. PEDUNCLES | 7 to 9 cm. |

| CULTIVAR | PLANT HEIGHT | FLOWERING RESPONSE PERIOD | LOW TEMPERATURE TOLERANCE |
|---|---|---|---|
| BRASS | MEDIUM 100 to 110 cm. | 9 WEEKS | 13° C. MIN. |
| FLAME BELAIR | TALL 120 to 130 cm. | 9 WEEKS | 16° C. MIN. |

COMPARISONS MADE OF PLANTS GROWN AS SINGLE STEM CUT SPRAY MUMS WITH 14 LONG DAYS IN SALINAS, CALIFORNIA

I claim:

1. A new and distinct plant of *Chrysanthemum morifolium,* Ramat., named Brass, as described and illustrated, and particularly characterized as to uniqueness by the combined characteristics of flat capitulum form; decorative capitulum type; greyed-orange ray floret color; diameter across face of capitulum ranging from 6 to 7 cm. at maturity; uniform nine week flowering response; medium plant height when grown single stem; 10 to 15 cm. peduncles on open, normally terminal sprays, and 13° C. minimum temperature tolerance for initiation and development of flowering buds.

* * * * *